US011414637B2

United States Patent
Tanaka et al.

(10) Patent No.: US 11,414,637 B2
(45) Date of Patent: Aug. 16, 2022

(54) CELL CULTURE VESSEL, SUPPORT JIG FOR CELL CULTURE VESSEL AND CELL CULTURE METHOD

(71) Applicant: TOYO SEIKAN GROUP HOLDINGS, LTD., Tokyo (JP)

(72) Inventors: Satoshi Tanaka, Kanagawa (JP); Ryo Suenaga, Kanagawa (JP); Takahiko Totani, Kanagawa (JP)

(73) Assignee: TOYO SEIKAN GROUP HOLDINGS, LTD., Tokyo (JP)

( * ) Notice: Subject to any disclaimer, the term of this patent is extended or adjusted under 35 U.S.C. 154(b) by 0 days.

(21) Appl. No.: 16/148,229

(22) Filed: Oct. 1, 2018

(65) Prior Publication Data
US 2019/0031994 A1     Jan. 31, 2019

Related U.S. Application Data

(63) Continuation of application No. PCT/JP2017/012265, filed on Mar. 27, 2017.

(30) Foreign Application Priority Data

Mar. 31, 2016 (JP) .............................. JP2016-070718
Oct. 25, 2016 (JP) .............................. JP2016-208335

(51) Int. Cl.
   *C12M 1/04*              (2006.01)
   *C12M 1/32*              (2006.01)
   (Continued)

(52) U.S. Cl.
CPC .............. *C12M 23/24* (2013.01); *C12M 1/00* (2013.01); *C12M 1/04* (2013.01); *C12M 23/04* (2013.01);
(Continued)

(58) Field of Classification Search
CPC .......... C12M 1/00; C12M 1/04; C12M 23/04; C12M 23/08; C12M 23/12; C12M 23/24; C12M 23/26
(Continued)

(56) References Cited

U.S. PATENT DOCUMENTS 5,362,642 A * 11/1994 Kern .................... B67D 7/0288
                                                             222/94
7,560,274 B1     7/2009 Fuller et al.
(Continued)

FOREIGN PATENT DOCUMENTS

FR           2519020 A1 * 7/1983 ............ C12M 23/14
JP           2004201689 A     7/2004
(Continued)

OTHER PUBLICATIONS

Vlcek et al., English machine translation of FR 2519020 A1 (Year: 1983).*
(Continued)

*Primary Examiner* — Liban M Hassan
(74) *Attorney, Agent, or Firm* — Osha Bergman Watanabe & Burton LLP

(57) ABSTRACT

A cell culture container includes a container main body comprising a gas-permeable plastic film, and an injection/discharge port. A peripheral portion of the container main body is sealed, and the container main body has a bulging shape on a top surface side of the container main body. A plurality of concave portions serving as cell culture parts are provided on a bottom surface of the container main body.

9 Claims, 3 Drawing Sheets

(51) Int. Cl.
*C12M 1/00* (2006.01)
*C12M 1/12* (2006.01)
*C12M 1/24* (2006.01)

(52) U.S. Cl.
CPC ............ *C12M 23/08* (2013.01); *C12M 23/12* (2013.01); *C12M 23/26* (2013.01)

(58) Field of Classification Search
USPC .......................................... 435/289.1, 297.5
See application file for complete search history.

(56) References Cited

U.S. PATENT DOCUMENTS

| | | | | |
|---|---|---|---|---|
| 2004/0132177 A1* | 7/2004 | Heron | ..................... | B29C 51/14 435/297.5 |
| 2010/0184182 A1* | 7/2010 | Hase | ...................... | C12M 21/08 435/173.1 |
| 2014/0011269 A1 | 1/2014 | Sakura et al. | | |
| 2014/0322806 A1* | 10/2014 | Bennett | ................. | C12M 23/02 435/325 |
| 2015/0140652 A1* | 5/2015 | Sasai | ...................... | C12M 23/20 435/366 |

FOREIGN PATENT DOCUMENTS

| | | |
|---|---|---|
| JP | 2005-295904 A | 10/2005 |
| JP | 2006-055069 A | 3/2006 |
| JP | 2009-011260 A | 1/2009 |
| JP | 2011-241159 A | 12/2011 |
| JP | 2014128247 A | 7/2014 |
| JP | 2015-116150 A | 6/2015 |
| JP | 2016-007170 A | 1/2016 |
| WO | 2012/133514 A1 | 10/2012 |
| WO | WO-2013183777 A1 * 12/2013 ........... C12N 5/0606 |  |

OTHER PUBLICATIONS

Beihaku Kanemura et al., English machine translation of JP 2006-055069 A . (Year: 2006).*
Kato Yoichi et al., English machine translation of JP 2009-011260 A . (Year: 2009).*
Kato et al., English machine translation of JP2009-011260 A. (Year: 2009).*
International Search Report issued in International Application No. PCT/JP2017/012265; dated May 23, 2017 (2 pages).
International Preliminary Report on Patentability issued in International Application No. PCT/JP2017/012265; dated Oct. 11, 2018 (12 pages).
Partial Supplementary European Search Report issued in European Application No. 17774872.0, dated Nov. 4, 2019 (12 pages).
Office Action issued in corresponding Korean Application No. 20187022886 dated Jan. 14, 2020, and English translation thereof (10 pages).
Office Action issued in corresponding Japanese Application No. 2016-208335; dated Sep. 1, 2020 (16 pages).

* cited by examiner

CELL CULTURE VESSEL, SUPPORT JIG FOR CELL CULTURE VESSEL AND CELL CULTURE METHOD

FIELD

One or more embodiments of the present invention relate to a cell culture container, a support jig for a cell culture container, and a cell culture method to efficiently culture various cells.

BACKGROUND

In recent years, efficient culture and differentiation-induction of a large amount of cells (comprising tissues, microorganisms, viruses, and the like) in an artificial environment have been requested in the production of medicine or in fields such as gene therapy, regenerative medicine, and immunotherapy.

In such cell culture, it is necessary to maintain cell density in a culture medium within a proper range. That is, if cell density in a culture medium increases along with the proliferation of cells, growth of cells is blocked by the depletion of culture medium components necessary for proliferation, the accumulation of metabolic products of the cells themselves, and the like, leading to deterioration in the proliferation efficiency of cells. Moreover, if cell density in a culture medium is too low, it is also impossible to efficiently culture cells and induce the differentiation thereof. Thus, when cells are cultured on a certain scale, culture is generally conducted with repeated passage so that proper cell density in a culture medium is maintained.

Heretofore, for subculture, a well plate, a flask, or the like has been often used as a culture container. For example, it is known to culture a large amount of cells as follows. Cells are added to individual wells together with a culture medium so as to achieve proper cell density, culture is thus started by use of a well plate, and cells are sufficiently proliferated in the wells and then transferred to a flask, a culture medium is added depending on the proliferation of cells, and culture is continued. At the point where cells have proliferated to a certain amount, passage is repeated by transferring cells to a flask having a larger capacity and further adding a culture medium (e.g., see Japanese Unexamined Patent Application Publication No. 2011-241159 ("PATENT LITERATURE 1"), paragraph [0027], and the like).

It is to be noted that, as a flask type culture container, Japanese Unexamined Patent Application Publication No. 2006-55069 ("PATENT LITERATURE 2") suggests a flask type culture container having a plurality of concave portions provided on one surface of the container formed into the shape of a polyhedron such as a rectangular parallelepiped. In PATENT LITERATURE 2, an aggregate resulting from the unification of single cells is formed in a plurality of concave portions provided on a first culture surface and serving as first culture parts. This aggregate is transferred to a second culture part formed in a second culture surface in the container and having an area larger than the first culture part so that the aggregate becomes a larger aggregate.

However, in conducting subculture as above, it is necessary to repeat pipetting operations many times when cells are added to individual wells of a well plate or when cells are transferred to a flask from a well plate. Moreover, cells have to be transferred to a new culture container such as a flask at every passage, which forces troublesome work, and increases the risk of contamination by bacteria, viruses, and the like.

Furthermore, in the flask type culture container as in PATENT LITERATURE 2, gas is exchanged only when a cover closing an opening is removed and the opening is thus opened. Therefore, a sufficient amount of oxygen can not be supplied to cells being cultured, and the risk of contamination is unavoidable at the time of gas exchange as well. In addition, the flask type culture container having a limited capacity is unsuited to a culture of a large amount of cells on a certain scale beyond a laboratorial level.

SUMMARY

One or more embodiments of the present invention provide a cell culture container, a support jig for a cell culture container, and a cell culture method to reduce the risk of contamination while maintaining proper cell density during culture, and yet efficiently culture cells and induce the differentiation thereof in the same container.

A cell culture container according to one or more embodiments of the present invention comprises: a container main body comprising a gas-permeable plastic film; and an injection/discharge port, wherein the container main body is sealed at a peripheral portion thereof, and has a bulging shape on a top surface side of the container main body, and a plurality of concave portions serving as cell culture parts are provided on a bottom surface of the container main body.

Furthermore, a support jig for a cell culture container according to one or more embodiments of the present invention is a jig which supports the above-described cell culture container, and is able to support the bottom surface side of the container main body so as not to contact the concave portions.

Still further, a cell culture method according to one or more embodiments of the present invention is a cell culture method using the above-described cell culture container, and is a method comprising supporting the bottom surface side of the container main body so as not to contact the concave portions, then collecting cells in bottom parts of the concave portions, and thereby culturing the cells.

According to one or more embodiments of the present invention, it is possible to reduce the risk of contamination while maintaining proper cell density during culture, and yet efficiently culture cells in the same container.

BRIEF DESCRIPTION OF DRAWINGS

FIG. 1A is a plan view, FIG. 1B is a side view, and FIG. 1C is a bottom view.

FIG. 2A is a plan view, FIG. 2B is a side view, and FIG. 2C is a bottom view.

DETAILED DESCRIPTION

Hereinafter, one or more embodiments of the present invention will be described with reference to the drawings.

Figure 1C:
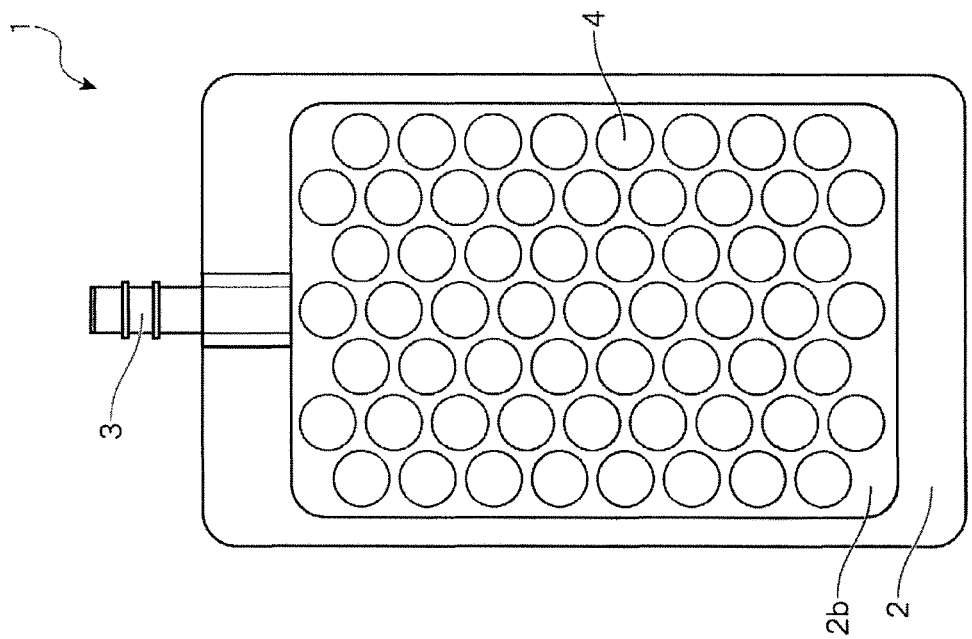
FIGS. 1A to 1C are explanatory diagrams showing an overview of a cell culture container according to one or more embodiments of the present invention.
Figure 1B:
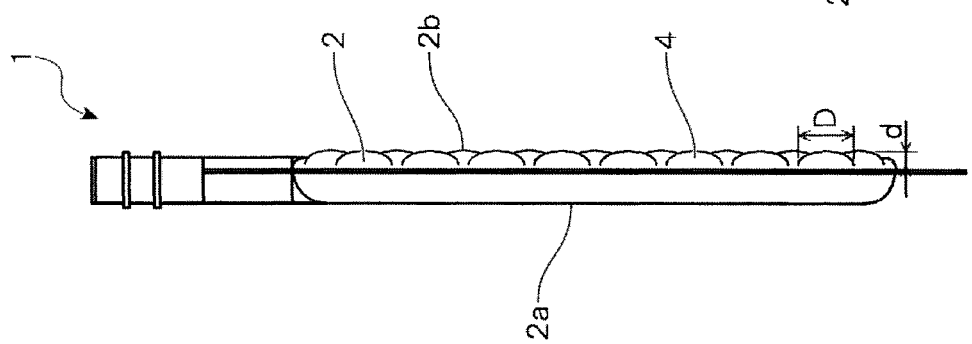
Figure 1A:
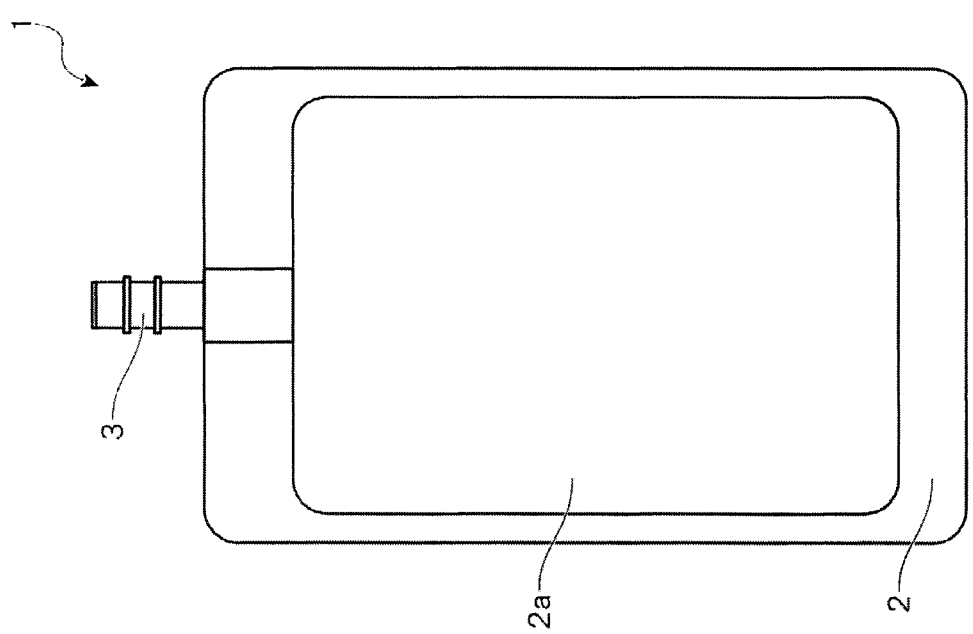

A cell culture container 1 shown in FIGS. 1A to 1C comprises a container main body 2 comprising a gas-permeable plastic film; and an injection/discharge port 3 comprising a tubular member through which a culture medium and cells can circulate.

The container main body 2 is sealed at a peripheral portion thereof, has a bulging shape in which a top surface 2a thereof is bulged like a plateau, and is formed so that a rim of the top surface 2a formed into a flat surface is inclined and connected to at the peripheral portion. In addition, a plurality of concave portions 4 serving as cell culture parts are provided on a bottom surface 2b of the container main body 2.

In order to inhibit the movement of cells in the container main body 2 so that cells being cultured remain in one concave portion 4, the concave portion 4 provided on the bottom surface 2b of the container main body 2 may have an opening diameter (diameter) D of 0.3 to 10 mm, 0.3 to 5 mm, 0.5 to 4 mm, or 0.5 to 2 mm, and a depth d of 0.1 mm or more. All of the concave portions 4 may have the same opening diameter. The concave portions 4 provided on the bottom surface 2b may comprise two or more kinds of concave portions different in opening diameter by dividing the bottom surface 2b into a plurality of regions so that the opening diameter of the concave portion 4 is different in each region, for example.

For example, in the present embodiment, the top surface 2a side of the container main body 2 is formed to be bulged like a plateau so that the rim of the top surface 2a is inclined and connected to the peripheral portion. Accordingly, the height of the peripheral portion side becomes lower. Therefore, when cells to be cultured are injected into the container main body 2 together with a culture medium, the amount of a culture medium comprising cells is smaller on the peripheral portion side, and the number of cells precipitating in the culture medium is also smaller. Thus, if all of the concave portions 4 have the same opening diameter, the number of cells precipitating into the concave portions 4 on the peripheral portion side becomes smaller. Therefore, it may be possible that the opening diameters of the concave portions 4 are larger on the peripheral portion side so that about the same number of cells precipitate into all of the concave portions 4.

Moreover, in the cell culture container 1 shown in FIGS. 1A to 1C, the shape of the concave portion 4 is a spherical crown shape so that cells are easily collected to the bottom of the concave portion 4. However, the shape of the concave portion 4 is not limited thereto. For cells to be easily collected to the bottom of the concave portion 4, it may be possible that a ratio d/D of the depth d to the opening diameter D of the concave portion 4 is 0.05 to 1.

Furthermore, in order to avoid the retention of cells in parts of the bottom surface 2b other than the concave portions 4, the area of the concave portions 4 occupying the bottom surface 2b may be as large as possible without deterioration of moldability, and specifically, may account for 30 to 90% of the area of the bottom surface 2b. Although the concave portions 4 may be arranged in a staggered form as shown so that the area of the concave portions 4 occupying the bottom surface 2b is as large as possible, the concave portions 4 may be arranged in a lattice form when necessary.

In addition, the size of the container main body 2 is not particularly limited, but may be, for example, 50 to 500 mm in length, and 50 to 500 mm in width.

Such a cell culture container 1 can be manufactured, for example, as follows.

First, a top surface side plastic film serving as the top surface 2a side of the container main body 2, and a bottom surface side plastic film serving as the bottom surface 2b side of the container main body 2 are prepared. Then, the top surface side plastic film is molded so as to bulge like a plateau other than at a peripheral portion thereof. On the other hand, a plurality of concave portions 4 are molded in the bottom surface side plastic film with a predetermined arrangement. The above can be formed by general vacuum molding, air pressure molding, or the like, and can be molded so that the bulging shape and the shape of the concave portion 4 are formed into desired shapes by suitably adjusting a die or the like.

Next, the top surface side plastic film and the bottom surface side plastic film that have been molded as above are laid on each other with that a tubular member to form the injection/discharge port 3 is interposed at a predetermined position, and sealed at the peripheral portions thereof by thermal welding. The peripheral portions are trimmed when necessary. Thereby, the cell culture container 1 as shown in FIGS. 1A to 1C can be manufactured.

In regard to the gas permeability of the plastic film that forms the container main body 2, the permeability of oxygen measured at a test temperature of 37° C. may be 5000 mL/(m$^2$·day·atm) or more in compliance with a gas permeability test method of JIS K 7126.

Moreover, it may be possible that the plastic film partly or entirely has transparency so that the progress of cell culture, the states of cells, and the like can be checked.

The material used for the plastic film that forms the container main body 2 is not particularly limited as long as the material has desired gas permeability. For example, the material includes thermoplastic resins such as polyethylene, polypropylene, ethylene-vinyl acetate copolymer, polyester, silicone-based elastomer, polystyrene-based elastomer, and tetrafluoroethylene-hexafluoropropylene copolymer (FEP). These materials may be used in a single layer, or materials of the same kind or different kinds may be used in a laminated layer. In consideration of heat fusion bonding properties during sealing the peripheral portion, a layer functioning as a sealant layer may be used.

Moreover, in order to have flexibility and yet have moderate shape maintaining properties that maintain the bulging shape of the top surface 2a side and the shape of the concave portion 4, the thickness of the plastic film used to form the container main body 2 may be 30 to 200 μm.

Furthermore, the injection/discharge port 3 comprises a tubular member through which a culture medium and cells can circulate, as described above. The tubular member that forms the injection/discharge port 3 can be molded into a predetermined shape by injection molding, extrusion molding, or the like, using a thermoplastic resin such as polyethylene, polypropylene, vinyl chloride, polystyrene-based elastomer, or FEP.

In addition, the injection/discharge port 3 can be provided with a port blocking prevention piece projecting into the container main body 2 from the proximal end of the injection/discharge port 3, in order to avoid blocking of the port due to the sticking of the top surface 2a side and the bottom surface 2b side of the container main body 2. When such a port blocking prevention piece is provided, the port blocking prevention piece may be provided to be located on the top surface 2a side of the container main body 2 so as not to prevent the precipitation of cells into the concave portions 4 provided on the bottom surface 2b.

When cell culture is conducted by use of such a cell culture container 1, cells to be cultured are injected into the container main body 2 together with a culture medium while a closed system is maintained via a liquid supply tube connected to the injection/discharge port 3. Then, the cells injected into the container main body 2 precipitate in the culture medium, and are thus collected to the bottom of each concave portion 4.

Herein, in a flat-pouch-shaped container in which two plastic films are laid on each other with a peripheral portion only sealed, the bottom surface is deformed so that the peripheral portion is lifted as the container is filled with content liquid. On the contrary, in the present embodiment, the top surface 2a side of the container main body 2 has a bulging shape, and it is possible to restrain the deformation of the bottom surface 2b during the injection of cells to be cultured together with a culture medium, by designing the bulging shape of the top surface 2a side in such a way as to consider an injection amount. This permits cells to be uniformly stored in each concave portion 4 without inclination or the like of the concave portions 4 provided on the bottom surface 2b.

In order for cells precipitating in the culture medium to be more easily collected to the bottom of each concave portion 4, it may be possible that the bottom surface 2b comprising the concave portions 4 is subjected to a cell low-adhesion treatment to make it difficult for cells to adhere. The cell low-adhesion treatment includes, for example, a treatment which gives hydrophilicity to the surface of the plastic film by a surface treatment such as a plasma treatment, and a treatment which blocks cell adhesive protein from sticking to the surface of the plastic film by coating with a phospholipid polymer, an interfacial active agent, protein such as albumin or the like.

Figure 2C:
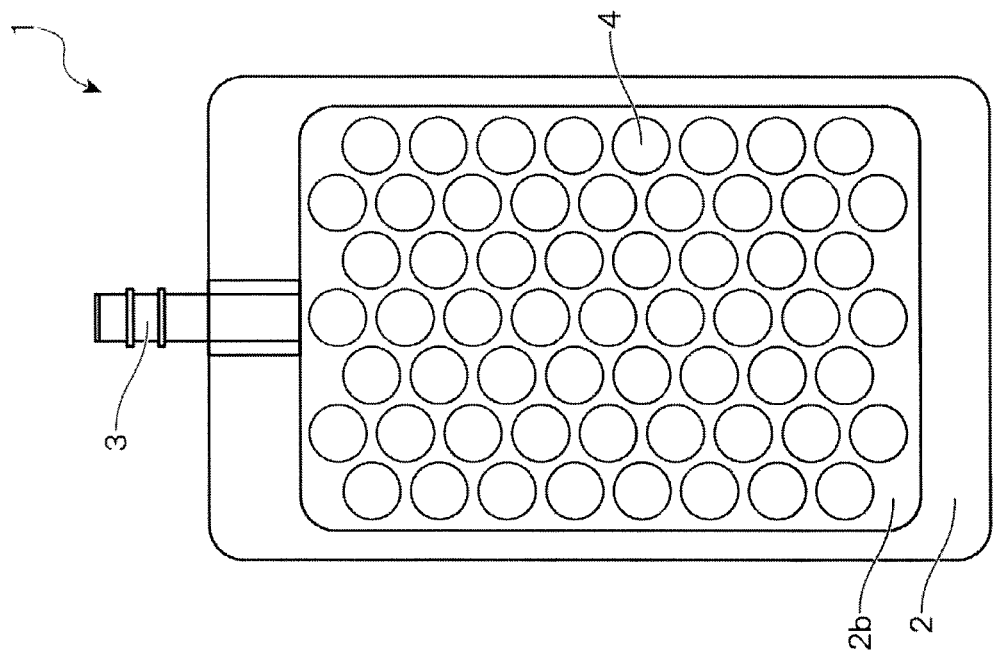
FIGS. 2A to 2C are explanatory diagrams showing an overview of a modification of the cell culture container according to one or more embodiments of the present invention.
Figure 2B:
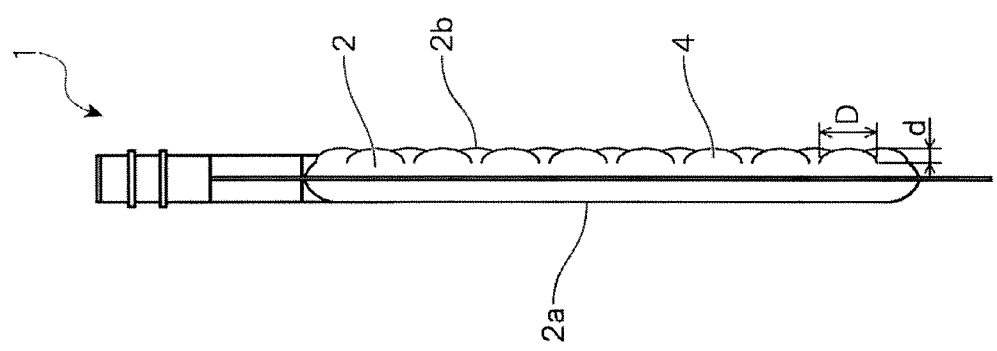
Figure 2A:
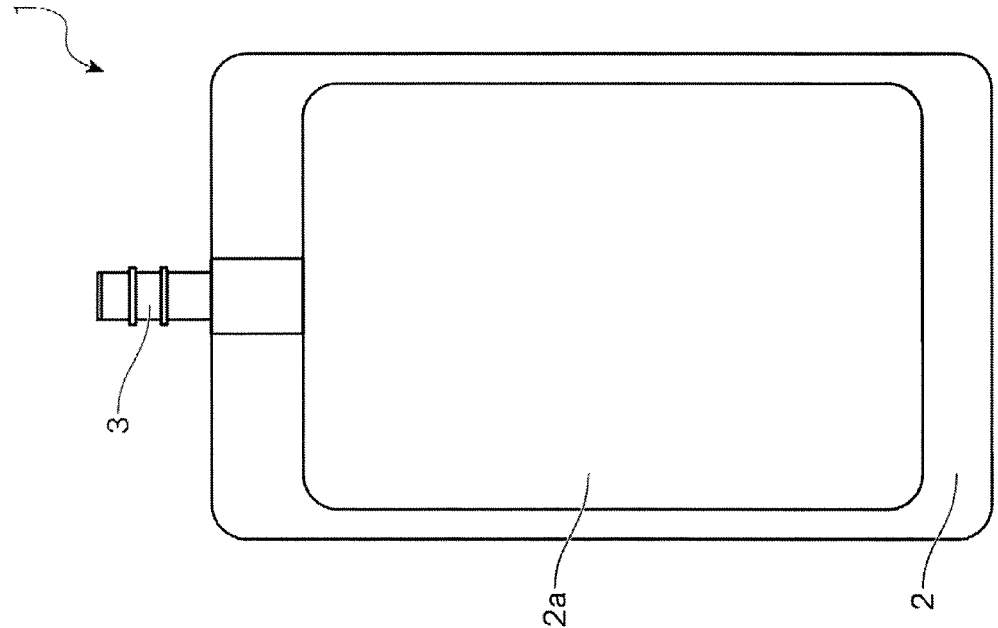

Furthermore, in order to avoid the retention of cells in parts of the bottom surface 2b other than the concave portions 4, particularly, on the peripheral portion side of the bottom surface 2b so that cells are more easily collected to the bottoms of the concave portions 4, the container main body 2 may have a bulging shape in which the bottom surface 2b side thereof is also bulged like a plateau in a manner similar to the top surface 2a side, as shown in FIGS. 2A to 2C. Consequently, the rim of the bottom surface 2b is formed so as to incline and connect to the peripheral portion, and the retention of cells on the peripheral portion side of the bottom surface 2b can be avoided. Moreover, in restraining the deformation of the bottom surface 2b during the injection of cells to be cultured together with a culture medium as well, it may be possible that the bottom surface 2b side of the container main body 2 also has a bulging shape.

It is to be noted that in the case of such an aspect, the bottom surface side plastic film needs only to be molded in a bulging form other than the peripheral portion thereof, and the concave portions 4 need only to be molded in the bulged part, when the cell culture container 1 is manufactured as described above.

Thus, according to the cell culture container 1 in the present embodiment, cells injected into the container main body 2 precipitate in the culture medium, and are thus collected to the bottom of each concave portion 4, and can be efficiently cultured and differentiation-induced in a state of increased cell density. In addition, the container main body 2 comprises a gas-permeable plastic film, and can therefore supply sufficient amount of oxygen to the cells being cultured. Particularly, in the present embodiment, it may be possible that when the concave portions 4 are molded in the bottom surface side plastic film as described above, the plastic film is extended so that the thickness of the concave portions 4 is smaller than the thickness of the parts of the bottom surface 2b other than the concave portions 4. This makes it possible to increase the gas permeability of the concave portions 4, and thus supply more sufficient oxygen to the cells collected in the concave portions 4.

Figure 3:
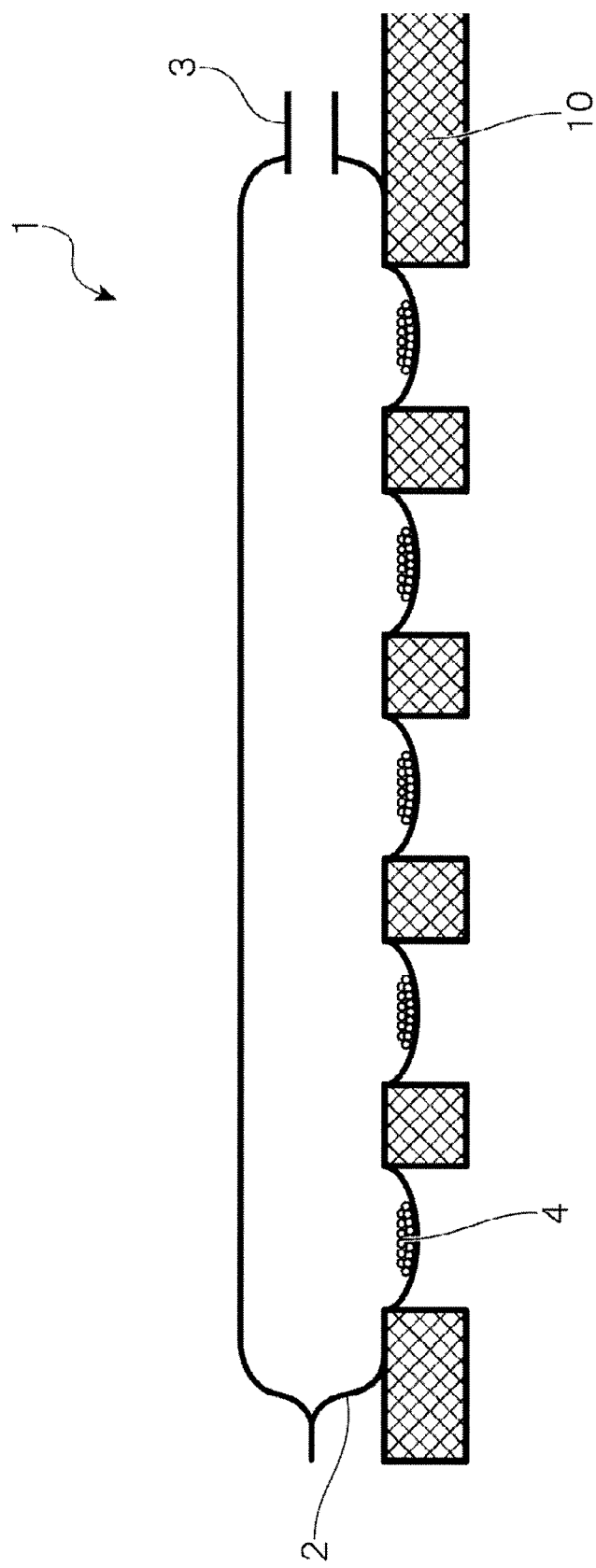
FIG. 3 is an explanatory diagram showing an example of the use of the cell culture container according to one or more embodiments of the present invention.

Furthermore, when cells are cultured by use of the cell culture container 1, cells can be cultured under a predetermined condition in an incubator such as a $CO_2$ incubator. In this instance, as shown in FIG. 3, the cell culture container 1 may be disposed on a table in the incubator via a jig 10 capable of supporting the bottom surface 2b side of the cell culture container 1 so as not to contact the concave portions 4. This makes it possible to certainly prevent the deformation of the concave portions 4 due to collapse or the like so that cells in a culture medium collected in the concave portions 4 do not flow out around the concave portions 4, and maximize gas permeability from the bottom surface 2b.

The jig 10 capable of supporting the bottom surface 2b side of the cell culture container 1 so as not to contact the concave portions 4 includes, for example, a flat-plate-shaped jig provided with a plurality of perforations or concave portions which correspond to the arrangement of the concave portions 4 and through which the concave portions 4 can be inserted without contact, and a wire-mesh-shaped jig in which a wire material is formed in a mesh shape between the concave portions 4 so as not to contact the concave portions 4.

Then, when cells collected to the bottoms of the concave portions 4 proliferate to a certain level or more and then the cell density thereof exceeds a range suited to culture, the top surface 2a is utilized as a culture surface by turning the cell culture container 1 upside down, and a culture area can be thereby enlarged. Thus, it is possible to continue cell culture while maintaining proper cell density in the same container It is to be noted that when cells to be cultured are anchorage-dependent cells, an enzyme solution to peel cells from the bottoms of the concave portions 4 is injected into the container main body 2 as needed at the time of turning the cell culture container 1 upside down. Even in this case, according to the present embodiment, it is possible to inject the enzyme solution into the container main body 2 while maintaining a closed system via the liquid supply tube connected to the injection/discharge port 3.

Furthermore, the culture of cells normally requires a period of several days to several weeks, and in this period, culture medium have to be added or exchanged as needed. In this case, according to the present embodiment, it is also possible to easily conduct such work while maintaining a closed system, by adding or exchanging culture medium via the liquid supply tube connected to the injection/discharge port 3. Moreover, after the end of culture, it is possible to collect cells in the cell culture container 1 while maintaining a closed system via the liquid supply tube connected to the injection/discharge port 3.

As described above, by conducting cell culture using the cell culture container 1 according to the present embodiment, it is possible to maintain proper cell density during culture while maintaining a closed system without conducting passage, and thus efficiently proliferate cells. Moreover, troublesome transfer work is not needed, the risk of contamination is reduced, and yet, cells can be efficiently cultured in the same container.

Furthermore, the container main body 2 is formed by use of a plastic film, and is therefore light and unbulky even if increased in volume. Thus, the container main body 2 is suited to the culture of a large amount of cells, and a sufficient amount of a cell medium can be injected into the container main body 2 in advance. In addition, the size of the container main body 2 can be adjusted by use of a clamp or the like, allowing flexible adaptation depending on the number of cells and the amount of a culture medium. In contrast, a flask type culture container as in PATENT LITERATURE 2 needs to be replaced with a container having a different size for adaptation.

While one or more embodiments of the present invention have been shown above to describe, the present invention is not limited to one or more embodiments described above, and it goes without saying that various changes can be made within the scope of the present invention. Those skilled in the art, having benefit of this disclosure, will appreciate that various other embodiments may be devised without departing from the scope of the present invention. Accordingly, the scope of the invention should be limited only by the attached claims.

For example, although the container main body 2 is rectangular and comprises, on one of the short sides thereof, the injection/discharge port 3 in one or more embodiments described above, the present invention is not limited thereto. The container main body 2 may have a quadrate shape, elliptical shape, circular shape, or the like in some cases, and can have various shapes as needed. The position where the injection/discharge port 3 is provided, and the number of the injection/discharge ports 3 can also be suitably changed.

The entire contents of the documents described in this specification, and the specification for the Japanese application which the present application is based upon and claims from under the Paris Convention are incorporated herein by reference.

One or more embodiments of the present invention can be utilized as a technique of efficiently culturing various cells.

What is claimed is:

1. A cell culture container comprising:
a container main body comprising a flexible gas-permeable plastic film; and
an injection/discharge port,
wherein a peripheral portion of the container main body is sealed,
wherein a plurality of concave portions serving as cell culture parts are provided on a bottom surface of the container main body,
wherein the container main body has a bulging shape like a plateau on a top surface side of the container main body so that the top surface is formed into a flat surface and a rim of the top surface is connected to the peripheral portion, whereby a deformation of the bottom surface while cells to be cultured are injected into the container main body together with a culture medium is restrained so as to inhibit inclination of the concave portions provided on the bottom surface,
wherein each of the plurality of concave portions has an opening diameter of 0.3 to 10 mm and a depth of 0.1 mm or more, and is configured to inhibit the movement of the cells in the container main body and to collect the cells in a bottom part of each of the concave portions in order to culture the cells,
and
wherein the flexible gas-permeable plastic film has a thickness of 30 to 200 µm and is capable to maintain the bulging shape and a shape of each of the concave portions through a flexibility of the film.

2. The cell culture container according to claim 1, wherein a total area of the plurality of concave portions occupying the bottom surface accounts for 30 to 90% of an area of the bottom surface.

3. The cell culture container according to claim 1, wherein the plurality of concave portions comprise two or more kinds of concave portions having different opening diameters.

4. The cell culture container according to claim 1, wherein the flexible gas-permeable plastic film has an oxygen permeability of 5000 mL/(m$^2$·day·atm) or more.

5. The cell culture container according to claim 1, wherein a thickness of the plurality of concave portions is smaller than a thickness of parts of the bottom surface other than the concave portions.

6. A support jig for the cell culture container according to claim 1, wherein the support jig is able to support a bottom surface side of the container main body without contacting the plurality of concave portions.

7. A cell culture method using the cell culture container according to claim 1, comprising:
supporting a bottom surface side of the container main body without contacting the plurality of concave portions; and
culturing cells while collecting the cells in bottom parts of the plurality of concave portions.

8. The cell culture container according to claim 1, wherein the flexible gas-permeable plastic film comprises polyethylene.

9. The cell culture container according to claim 1, wherein the plurality of concave portions are molded in the bottom surface of the container main body.

* * * * *